United States Patent
Wardenier et al.

(10) Patent No.: US 9,958,789 B2
(45) Date of Patent: May 1, 2018

(54) METHOD OF METROLOGY, INSPECTION APPARATUS, LITHOGRAPHIC SYSTEM AND DEVICE MANUFACTURING METHOD

(71) Applicant: ASML Netherlands B.V., Veldhoven (NL)

(72) Inventors: Peter Hanzen Wardenier, Eindhoven (NL); Frank Staals, Eindhoven (NL); Jean-Pierre Agnes Henricus Marie Vaessen, Echt (NL); Hans Van Der Laan, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days. days.

(21) Appl. No.: 15/186,031

(22) Filed: Jun. 17, 2016

(65) Prior Publication Data
US 2016/0370710 A1    Dec. 22, 2016

(30) Foreign Application Priority Data
Jun. 18, 2015   (EP) .................................... 15172709

(51) Int. Cl.
*G03F 7/20*      (2006.01)
*G01B 11/03*     (2006.01)
(52) U.S. Cl.
CPC .......... *G03F 7/70591* (2013.01); *G01B 11/03* (2013.01); *G03F 7/70616* (2013.01); *G03F 7/70625* (2013.01); *G03F 7/70633* (2013.01)
(58) Field of Classification Search
CPC . G01B 11/03; G03F 7/70591; G03F 7/70616; G03F 7/70625; G03F 7/70633
See application file for complete search history.

(56) References Cited

U.S. PATENT DOCUMENTS 7,433,039 B1    10/2008 Levinski et al.
2003/0021466 A1    1/2003 Adel et al.
(Continued)

FOREIGN PATENT DOCUMENTS

WO    WO 2012/062501 A1    5/2012
WO    WO 2013/178422 A1    12/2013
WO    WO 2016/096524 A1    6/2016

OTHER PUBLICATIONS

International Search Report and Written Opinion of the International Searching Authority directed to related International Patent Application No. PCT/EP2016/063145, dated Oct. 5, 2016; 10 pages.
(Continued)

*Primary Examiner* — Steven H Whitesell Gordon
(74) *Attorney, Agent, or Firm* — Sterne, Kessler, Goldstein & Fox P.L.L.C.

(57) ABSTRACT

Disclosed is a method of determining a correction for measured values of radiation diffracted from a target comprising a plurality of periodic structures, subsequent to measurement of the target using measurement radiation defining a measurement field. The correction acts to correct for measurement field location dependence in the measured values. The method comprises performing a first and second measurements of the periodic structures; and determining a correction from said first measurement and said second measurement. The first measurement is performed with said target being in a normal measurement location with respect to the measurement field. The second measurement is performed with the periodic structure in a shifted location with respect to the measurement field, said shifted location comprising the location of another of said periodic structures when said target is in said normal measurement location with respect to the measurement field.

19 Claims, 6 Drawing Sheets

(56) References Cited

U.S. PATENT DOCUMENTS

| | | |
|---|---|---|
| 2006/0033921 A1 | 2/2006 | Den Boef et al. |
| 2006/0066855 A1 | 3/2006 | Boef et al. |
| 2008/0212097 A1 | 9/2008 | Mos et al. |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0069337 A1 | 3/2012 | Ishigo |
| 2012/0123581 A1 | 5/2012 | Smilde et al. |
| 2012/0242970 A1 | 9/2012 | Smilde et al. |
| 2013/0100427 A1* | 4/2013 | Koolen .................. G03F 1/42 355/67 |
| 2013/0258310 A1 | 10/2013 | Smilde et al. |
| 2013/0271740 A1 | 10/2013 | Quintanilha |
| 2013/0286395 A1 | 10/2013 | Lee et al. |
| 2014/0204397 A1 | 7/2014 | Smilde et al. |

OTHER PUBLICATIONS

U.S. Appl. No. 15/184,898, filed Jun. 16, 2016 (Not Published).

* cited by examiner

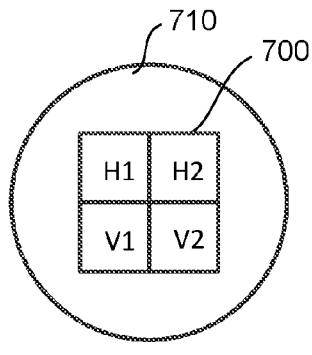
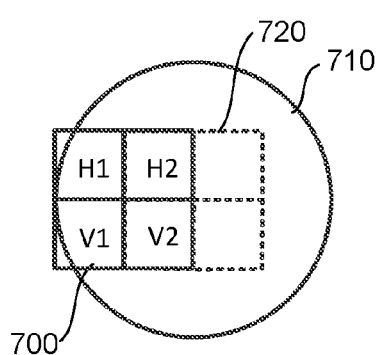
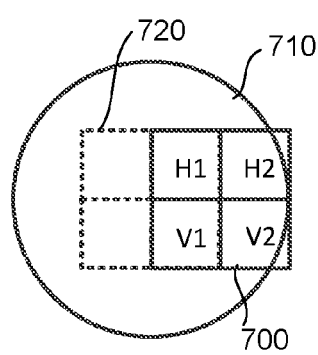
Fig. 7A        Fig. 7B        Fig. 7C
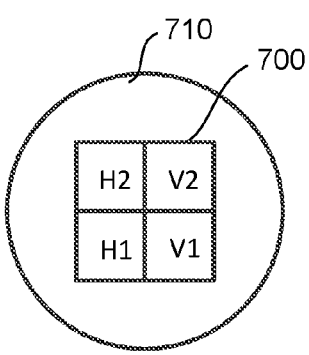
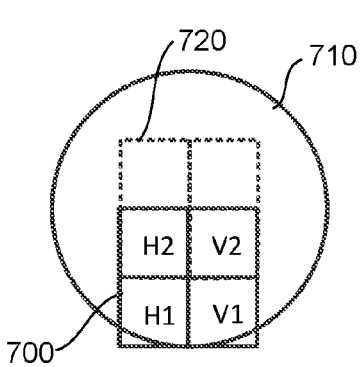
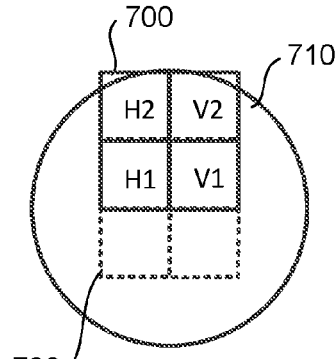
Fig. 7D        Fig. 7E        Fig. 7F
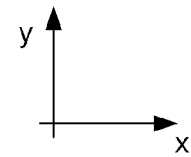

METHOD OF METROLOGY, INSPECTION APPARATUS, LITHOGRAPHIC SYSTEM AND DEVICE MANUFACTURING METHOD

BACKGROUND

Field of the Invention

The present invention relates to methods and apparatus for metrology usable, for example, in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large, e.g., 40 μm by 40 μm, gratings and the measurement beam generates a spot (measurement field) that is smaller than the grating (i.e., the grating is underfilled). In addition to measurement of feature shapes by reconstruction, diffraction based overlay or diffraction based focus can be measured using such apparatus, as described in published patent application US2006066855A1. Diffraction-based overlay and diffraction based focus metrology using dark-field imaging of the diffraction orders enables measurement of overlay, focus, dose and other parameters on smaller targets. These targets can be smaller than the measurement field and may be surrounded by product structures on a substrate. The intensities from the environment product structures can efficiently be separated from the intensities from the overlay target with the dark-field detection in the image-plane.

Examples of dark field imaging metrology can be found in patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20120242970A1, US20130258310A, US20130271740A and WO2013178422A1. Typically in these methods it is desired to measure asymmetry as a property of the target. Targets can be designed so that measurement of asymmetry can be used to obtain measurement of various performance parameters such as overlay, focus or dose. Asymmetry of the target is measured by detecting differences in intensity between opposite portions of the diffraction spectrum using the scatterometer. For example, the intensities of +1 and −1 diffraction orders may be compared, to obtain a measure of asymmetry.

In some of these prior patent applications, it is proposed to perform dark-field metrology using different illumination modes and/or different image detection modes to obtain the +1 and −1 diffraction orders from periodic structures (gratings) within the target. On the other hand, such methods are susceptible to asymmetry in the optical paths used in the different modes, which will result in errors when measuring the asymmetry of the target. Accordingly, although veracious calibrations and corrections can be applied to reduce these errors, it is generally the case that best overlay, focus or dose measurement results are obtained if the target is measured twice under identical conditions of illumination and detection. To do this, the substrate is rotated 180 degrees between measurements, to obtain the −1 and the +1 diffraction order intensities in turn. This mode of asymmetry measurement may therefore be referred to as a wafer rotation mode. The use of exactly the same optical path for both measurements ensures that any difference between the measured intensities is due to target properties, not properties of the scatterometer.

As an alternative to wafer rotation mode, which obviates the need to rotate the wafer, is complementary aperture mode. In complementary aperture mode, off-axis illumination from two opposite directions is used to obtain the −1 and the +1 diffraction order intensities in turn.

Dark field imaging metrology, in particular, may measure a target comprising multiple gratings, such that each grating is captured simultaneously in the same image. One problem with this is the issue of measurement field non-homogeneity. This measurement field non-homogeneity results in measured intensity values from the image having a measurement field location dependence.

SUMMARY OF THE INVENTION

It is desirable to provide a method and apparatus for determining a correction factor for said measurement field location dependence.

The invention provides a method of determining a correction for measured values of radiation diffracted from a target subsequent to measurement of the target using measurement radiation defining a measurement field, said correction correcting for measurement field location dependence in said measured values, said target comprising a plurality of periodic structures; wherein said method comprises: performing a first measurement and a second measurement of at least one of said periodic structures; and determining a correction from said first measurement and said second measurement; wherein said first measurement is performed with said target being in a normal measurement location with respect to the measurement field; and said second measurement is performed with the periodic structure in a shifted location with respect to the measurement field, said shifted location comprising the location of another of said periodic structures when said target is in said normal measurement location with respect to the measurement field The invention further provides a computer program product comprising machine readable instructions for causing a programmable processing device to implement a method according to the invention as set forth above. The machine readable instructions may be embodied for example in a non-transitory storage medium.

The invention further provides a lithographic system including a lithographic apparatus and an inspection apparatus according to the invention, as set forth above.

The invention further provides a method of manufacturing devices wherein a device pattern is applied to a series of substrates using a lithographic process, the method including: using the method of the first aspect to determine at least one correction, applying the at least one correction to intensity measurements, and using the corrected intensity measurements to monitor a lithographic process parameter, and controlling the lithographic process for later substrates in accordance with the lithographic process parameter Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example, with reference to the accompanying drawings in which.

Figure 3A:
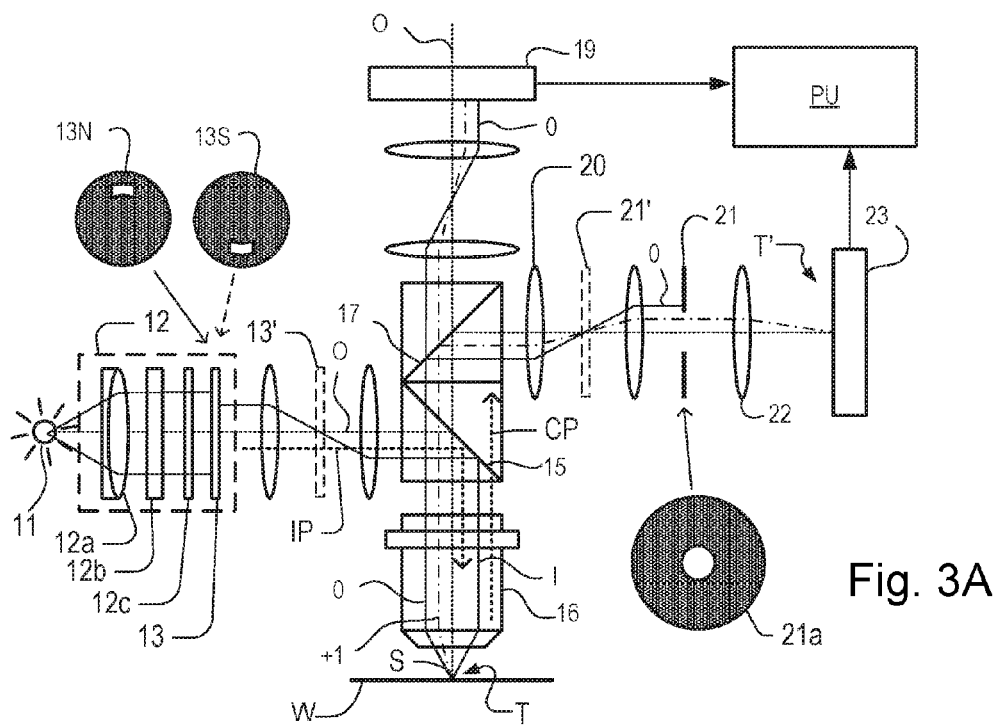
Figures 3B, 3C:
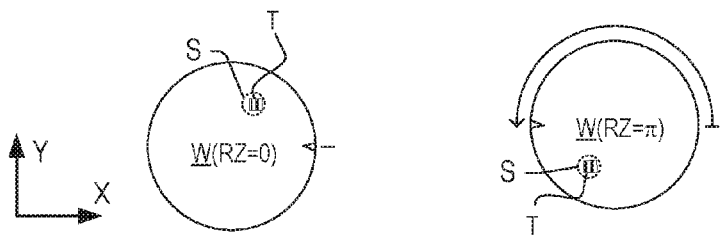
Figures 3D, 3E:
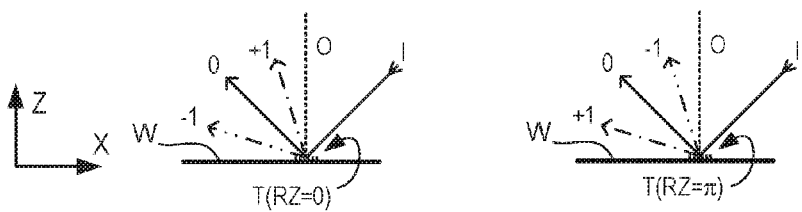
Figure 4A:
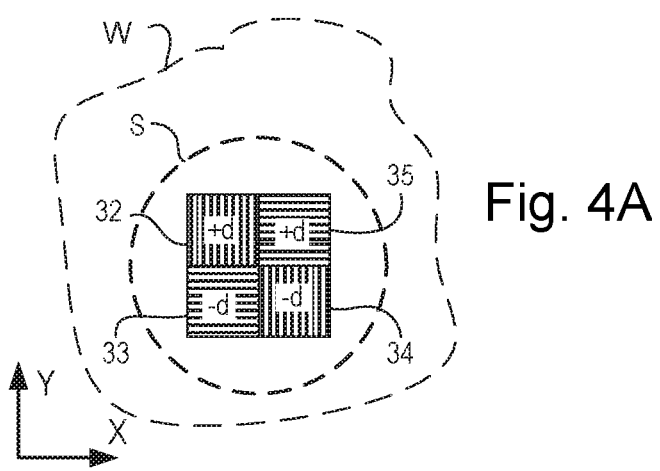
Figure 4B:
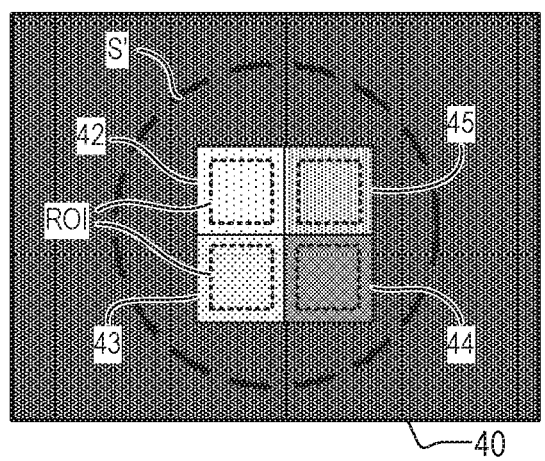
Figure 5:
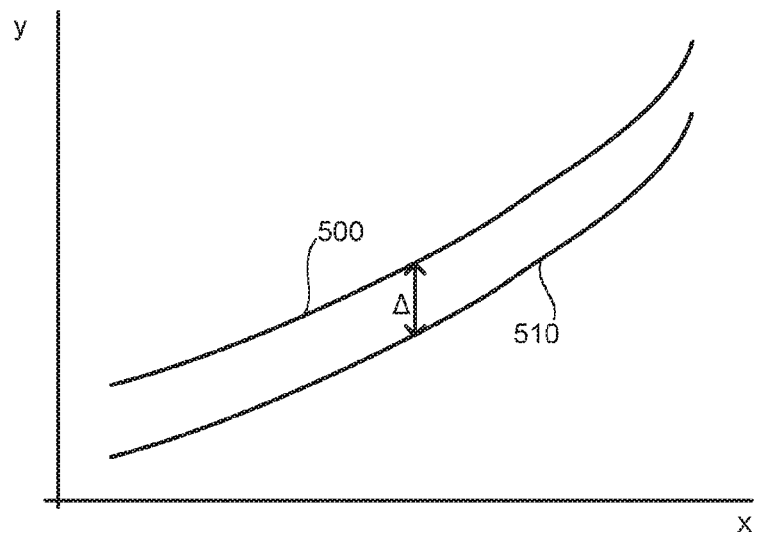
Figure 6A:
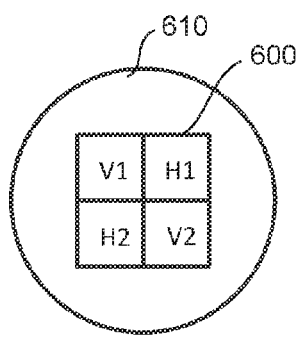
Figure 8:
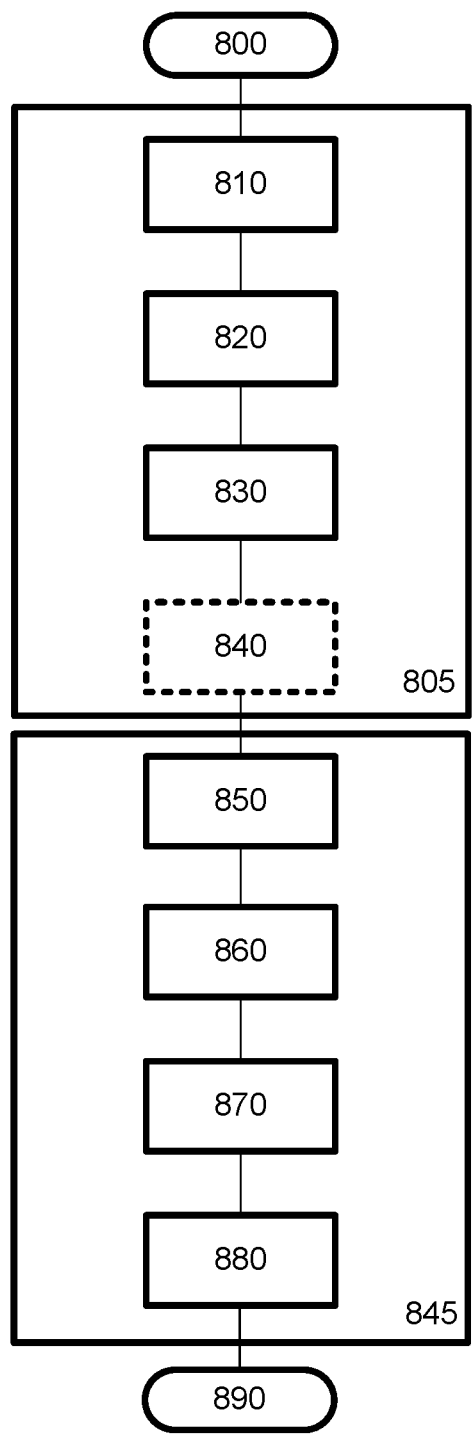

FIGS. 3A-3E comprise FIG. 3A a schematic diagram of an inspection apparatus according to a first embodiment of the invention, FIG. 3B representation of a substrate and target in a first orientation, FIG. 3C representation of the substrate and target in a second orientation, FIG. 3D schematic illustration of the capture of a +1 diffraction order with a substrate in the first orientation FIG. 3E and schematic illustration of capture of a −1 diffraction order with the substrate in the second orientation;

FIGS. 4A-4B depict FIG. 4A a known form of target and an outline of a measurement field on a substrate and FIG. 4B an image of the target obtained in the inspection apparatus of FIGS. 3A-3E;

FIG. 5 is a graph of intensity or asymmetry on the y-axis against a parameter of interest (e.g., focus, dose or overlay) on the x-axis for a grating measured in two locations relative to the measurement field;

FIGS. 6A-6E illustrate FIG. 6A a first measurement of a target in a normal location and FIGS. 6B-6E a second measurement of each grating in a shifted location;

FIGS. 7A-7F illustrate FIG. 7A and FIG. 7D a first measurement of a target in a normal location; and FIG. 7B, FIG. 7C, FIG. 7E and FIG. 7F a second measurement of each grating in a shifted location; and FIG. 8 is a flowchart describing a method of an embodiment of the invention.

DETAILED DESCRIPTION

Before describing embodiments of the invention in detail, it is instructive to present an example environment in which embodiments of the present invention may be implemented.

Figure 1:
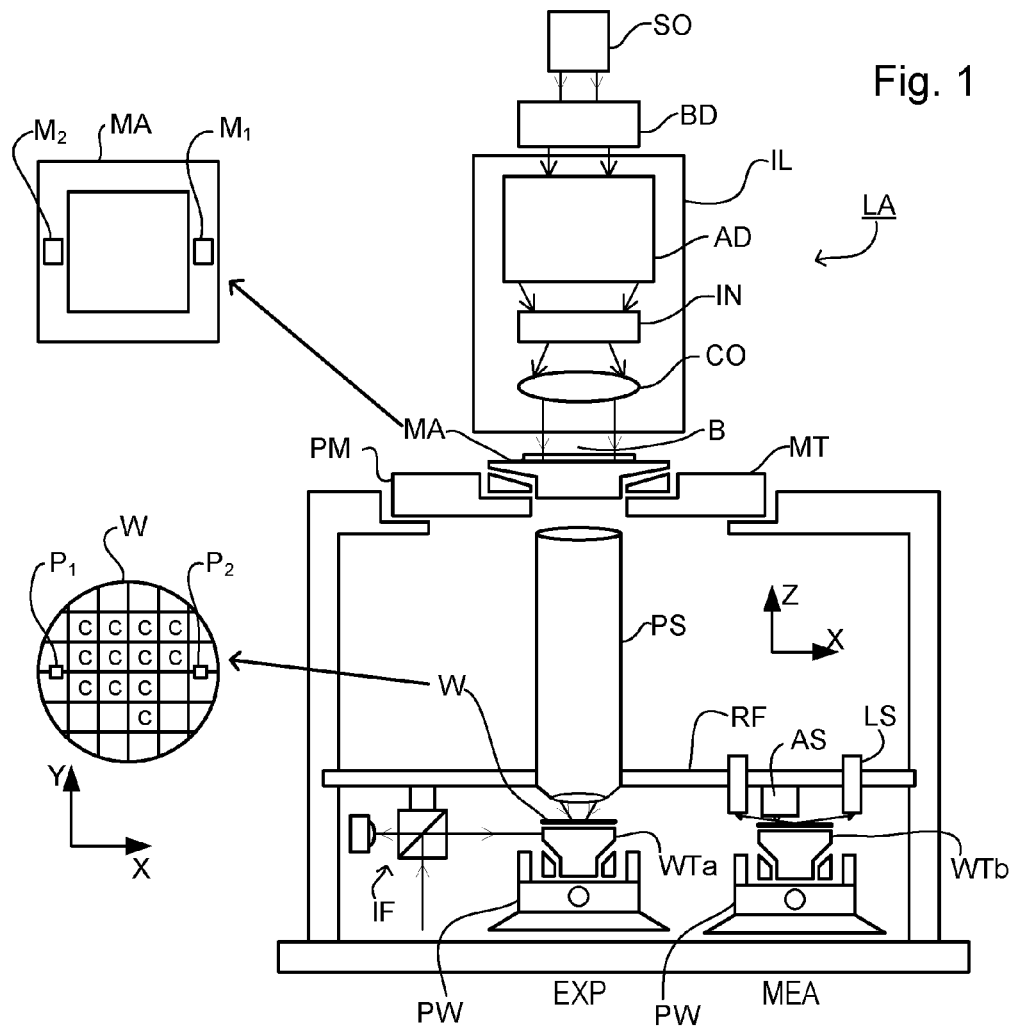
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can take many forms, The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
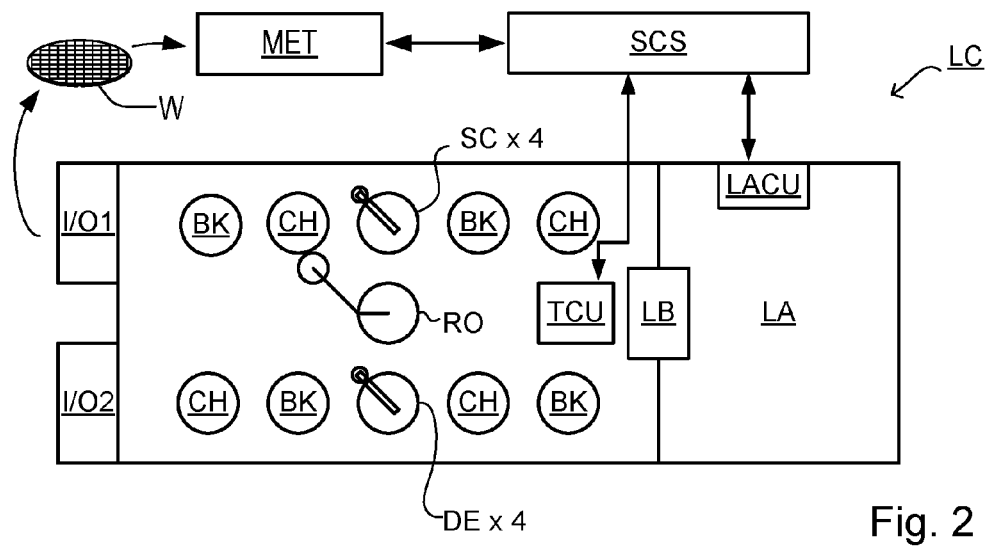
FIG. 2 depicts a lithographic cell or cluster including an inspection apparatus according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, exposure focus and dose, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Example Inspection Apparatus for Small Target Dark Field Metrology

An inspection apparatus adapted to perform dark field metrology is shown in FIG. 3A. A substrate W with target T is shown in different orientations in FIG. 3B and FIG. 3C. A periodic structure or grating of target T and diffracted rays are illustrated in more detail in FIGS. 3D and 3E. The dark field metrology apparatus may be a stand-alone device or incorporated in either the lithographic apparatus LA, e.g., at the measurement station, or the lithographic cell LC.

In this type of inspection apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 (a beam splitter) and focused into a spot (measurement field) S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired.

When the radiation beam is incident on the partially reflecting surface 15, part of it is transmitted through the beam splitter and follows a reference path (not shown). Radiation in the reference path is detected for example to measure the intensity of the incident radiation, to allow normalization of the intensity values measured in the scatter spectrum (diffraction spectrum).

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and is instead re-imaged with auxiliary optics (not shown) onto the detector located in a so-called conjugate pupil plane P'. The detector is preferably a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation.

The various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 12c may be rotatable or swappable so as to implement different polarization states in the measurement field S. Aperture device 13 can be adjusted to implement different illumination profiles, as described further below. Aperture device 13 is located in a plane P''' conjugate with pupil plane P of objective lens 16 and the plane of the detector 19. In this way, an illumination profile defined by the aperture device defines the angular distribution of light incident on substrate radiation passing through different locations on aperture device 13.

A second beam splitter (partially reflecting surface) 17 divides the diffracted beams into two measurement branches. In a first measurement branch, optical system 18 forms a diffraction spectrum (pupil plane image) of the target on first detector 19 (e.g. a CCD or CMOS sensor) using the zeroth and first order diffractive beams, as described above. In the second measurement branch, an optical system including lenses 20, 22 forms an image of the target on the substrate W on a second two-dimensional image detector 23 (e.g. a CCD or CMOS sensor). In the second measurement branch, an aperture plate referred to as field stop 21 is provided in a plane that is conjugate to the pupil-plane. This plane can be referred to as an 'intermediate pupil plane'. Field stop 21 functions to block the zeroth order diffracted beam so that the image of the target formed on detector 23 is formed only from the −1 or +1 first order beam. The images captured by detectors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

Where a metrology target T is provided on substrate W, this may be a 1-D periodic structure or grating, which is printed such that after development, the bars are formed of solid resist lines. The target may be a 2-D periodic structure or grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS. Illumination symmetry and the presence of such aberrations will manifest themselves in a variation in the printed grating. Accordingly, the scatterometry data of the printed gratings is used to measure properties of the gratings. These properties in turn are used to monitor the properties of functional product features formed by the same process, elsewhere on the substrate.

In a particular application of the apparatus, processes are monitored by measurement of asymmetry of features in product and/or target patterns. A particular application of asymmetry measurement is for the measurement of overlay, where the target comprises one set of periodic features superimposed on another. Simply stated, while the positions of the diffraction orders in the diffraction spectrum of the target are determined only by the periodicity of the target, asymmetry of intensity levels in the diffraction spectrum is indicative of asymmetry in the individual features which make up the target. Another application of asymmetry measurement is to measure from an exposed target, values that were set for focus or dose during the exposure of the target.

In the first measurement branch, such asymmetry in the diffraction orders appears directly as asymmetry in the pupil image recorded by detector 19. This asymmetry can be measured by digital image processing in unit PU, and calibrated against known values of overlay, focus or dose (for example). For the present disclosure, however, of greatest interest is measurement of asymmetry on small targets by a dark-field imaging technique, using a second measurement branch of the apparatus, as will now be described (although applicability to pupil plane measurements using the first measurement branch are not excluded from this disclosure).

As mentioned, the angular range at which the radiation is incident on the substrate can be selected by defining a spatial intensity distribution in a plane that presents the spatial spectrum of the substrate plane, here referred to as a (conjugate) pupil plane. In particular, this can be done by providing an aperture device 13 of suitable form between lenses 12 and 14, in a plane which is a back-projected image of the objective lens pupil plane. In the example illustrated, changing aperture device 13 allows different apertures, and hence different illumination modes, to be selected. The illustrated form of aperture 13N defines an off-axis illumination from a direction designated, for the sake of description only, as 'north'. In a second illumination mode, aperture 13S is used to provide similar illumination, but from an opposite direction, labeled 'south'. Other modes of illumination are possible by using different apertures. The rest of the pupil plane is desirably dark, as any unnecessary light outside the desired illumination mode will interfere with the desired measurement signals.

As shown schematically in FIG. 3B and FIG. 3C, measurement field (also referred to as measurement spot) S can be placed onto target T with the target in different orientations. To achieve this, a substrate table may be provided to hold the substrate W during measurement operations. The substrate tables may be similar or identical in form to the substrate tables WTa, WTb in the lithographic apparatus LA, of FIG. 1. (In an example where the inspection apparatus is integrated with the lithographic apparatus, they may even be the same substrate tables.) Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. Rotation of the substrate table about the Z axis is also provided for. It is convenient to think and describe operations as if the measurement field S is being brought to different locations on the substrate. In the practical implementation of these operations, it is usually more convenient if the optical system remains substantially stationary while the substrate moves. Provided the relative position of the substrate and the optical system is correct, it does not matter in principle whether one or both of those is moving in the real world.

In FIG. 3B, we see an example target T brought into measurement field S in a first orientation, which we can define by a rotation angle RZ of zero degrees (RZ=0). In FIG. 3C we see the same target brought into measurement field S with a rotation of 180 degrees (RZ=π in radians). It will be understood that the sizes of measurement field and target here are greatly exaggerated for the sake of illustration. A real substrate may have many targets distributed across it, for measuring overlay and other parameters at different positions on the substrate. The diameter of measurement field S may be for example between 10 and 50 μm, while the target T fits within the measurement field diameter in this type of small target metrology. The target is thus referred to as "overfilled".

FIGS. 3D and 3E show schematically more detail of the diffraction spectrum that results when a periodic structure (grating) of target T is placed into measurement field S with substrate W normal to the optical axis O of objective lens 16. In FIG. 3D the orientation RZ=0 is used, while in FIG. 3E the 180 degree rotated orientation is used (RZ=π). A ray of illumination I impinging on grating T from an angle off the axis O gives rise to a zeroth order ray (solid line 0) and two first order rays (single dot-dash line +1 and double dot-dash line −1).

It should be remembered that each of the rays illustrated is just one of many parallel rays falling on the area of the substrate which includes metrology target T and, with an overfilled small target grating, may include other features unrelated to the measurement process. Since the aperture in plate 13 has a finite width (necessary to admit a useful quantity of light) the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIG. 3A, FIG. 3D and FIG. 3E are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3A, both the first and second illumination modes are illustrated, by designating diametrically opposite apertures labeled as north (13N) and south (13S). When the incident ray I is from the north side of the optical axis, that is when the first illumination mode is applied using aperture plate 13N, the +1 diffracted rays, which are labeled +1, enter the objective lens 16 when the orientation of the target is the first orientation (RZ=0). In contrast, in the second orientation (RZ=π)−1 diffracted rays are the ones which enter the lens 16.

A measurement of asymmetry A can be calculated from the intensities of a first selected part of radiation diffracted by a grating and a second selected part of radiation diffracted by a grating, and more specifically from the intensities of detected radiation for the +1 and −1 diffraction orders. In the formula:

$$A = I_{+1} - I_{-1} \quad \text{Equation (1)}$$

the asymmetry measurement is calculated as a difference between intensities measured for the +1 and −1 orders. For each intensity measurement I, a subscript denotes the diffraction order +1 or −1 (other, higher orders can be used instead of the first orders).

Which portion of the diffraction spectrum is used in formation of an image on detector 23 is a function of the illumination aperture, the field stop, the radiation wavelength and the pitch of the periodic structure(s) within the measurement field. The particular forms of aperture plate 13 and field stop 21 shown in FIG. 3 are purely examples. Another way to change which portion of the diffraction spectrum enters objective lens 16 without changing the orientation of the target is to change the illumination mode, for example by changing from aperture 13N to aperture 13S. This option can be used in the methods, explained below. Further alternatives are to change the field stop 21, instead of or in addition to changing the aperture 13. In other embodiments of the invention, some of which will be illustrated and described below, on-axis illumination of the targets is used and a field stop with an off-axis aperture is used to pass substantially only one first order of diffracted light to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial light modulator can be used also. Moving mirrors or prisms can be used as another way to adjust the illumination mode.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3C and 3D which can be used as described further below. For the time being, it is sufficient to consider simply that the aperture plate 13N is used.

FIG. 4A depicts a composite target formed on a substrate according to known practice. The composite target comprises four gratings 32 to 35 positioned closely together so that they will all be within a measurement field S formed by the illumination beam of the metrology apparatus and thus are all simultaneously illuminated and simultaneously imaged on detector 23. In an example dedicated to overlay measurement, gratings 32 to 35 are themselves composite gratings formed by overlying gratings that are patterned in different layers of the semiconductor product formed on substrate W. Gratings 32 to 35 are differently biased in order to facilitate measurement of overlay between the layers in which the different parts of the composite gratings are formed. Also in this example, gratings 32 and 34 have periodicity and overlay bias in the X direction, while gratings 33 and 35 have orientation and overlay bias in the Y direction. In one example, gratings 32 to 35 have biases of +d, −d, −d, +d respectively. Bias +d means that one of the gratings has its components arranged so that if they were both printed exactly at their nominal locations one of the components would be offset relative to the other by a distance d. A bias −d means that an overlay grating has its components arranged so that, if perfectly printed, there would be an offset of d but in the opposite direction to the first grating and so on. While four gratings are illustrated, a practical embodiment might require a larger matrix to obtain the desired accuracy. For example, a 3×3 array of nine composite gratings may have biases −4d, −3d, −2d, −d, 0, +d, +2d, +3d, +4d. Separate images of these gratings can be identified in the image captured by detector 23.

FIG. 4B shows an example of an image that may be formed on and detected by the detector 23, using the target of FIG. 4 in the apparatus of FIG. 3. While the pupil image detector 19 cannot resolve the different individual gratings 32 to 35, the field image detector 23 can do so. The dark rectangle labeled 23 represents the field of the image on the detector 23, within which the measurement field S on the substrate is imaged into a corresponding circular area S'. Within this, rectangular areas 42-45 represent the images of the small target gratings 32 to 35. If the gratings are located in product areas, product features may also be visible in this image. Image processor and controller PU processes these images to identify the separate images 42 to 45 of gratings 32 to 35. This can be done by pattern matching techniques, so that the images do not have to be aligned very precisely at a specific location within the sensor frame. Reducing the need for accurate alignment in this way greatly improves throughput of the measuring apparatus as a whole. However, positional variation may introduce inaccuracies in the measurement results, if the imaging process is subject to non-uniformities across the measurement field. Not only properties of the various components in the optical path, but also intensity of illumination and sensitivity of detection can vary across the measurement field.

Once the separate images of the gratings have been identified, the intensities of those individual images can be measured, e.g., by averaging or summing selected pixel intensity values within the identified areas. Intensities and/or other properties of the images can be compared with one another, for example using Equation (1). These results can be combined to measure different parameters of the lithographic process. Overlay performance, focus and/or dose, each of which can be measured by measuring asymmetry of a grating target, are important examples of such a parameter.

Different targets can be designed so that their asymmetry depends strongly on a parameter of interest for measurement of the lithographic process. For the examples described herein, the target may be designed (by way of example) for measurement of overlay or of focus and/or dose as a parameter of interest. A measurement of overlay OV in the vicinity of this target can be calculated as a function of the asymmetries measured for two or more gratings, using knowledge of the different bias values they contain:

$$OV = f(A_{-d}, A_{+d}) \quad \text{Equation (2)}$$

That is to say, the unknown overlay OV can be calculated using measurements of asymmetry of biased gratings, combined with knowledge of the different biases in the gratings. Noting that the example target of FIG. 3A is a composite target with component gratings in X and Y directions, and having two bias values +d and −d, it will be understood that the target allows measurements of overlay in both X and Y directions to be calculated from measurements of asymmetry of those target gratings. In one example, overlay is calculated by the formula:

$$OV = \frac{p}{2\pi} \cdot \operatorname{atan}\left(\tan\left(\frac{2\pi d}{p}\right) \cdot \frac{A_{+d} + A_{-d}}{A_{+d} - A_{-d}}\right), \quad \text{Equation (3)}$$

where d is the amount of bias and p is the grating pitch. Bias and pitch may be expressed for example in nanometers (nm).

Another particular application of asymmetry measurement is for the measurement of focus and/or dose from gratings which print with a focus and/or dose dependent asymmetry. In this regard, gratings can be designed for which asymmetry of a grating structure is sensitive to variations in focus during an exposure step of the lithographic process. Knowing the relationship between focus and asymmetry, in particularly by using gratings with different bias values for their sensitivity, focus measurements can be derived by observing asymmetry in gratings of this type. Similarly, gratings can be devised in which asymmetry is sensitive to the dose variations in the lithographic process. Using such gratings, dose variations across the substrate or between substrates can be measured based on measurements of asymmetry of the type already described. All these different types of gratings can be provided on the same substrate and even within the same composite target, if desired, to provide comprehensive information on the performance of the lithographic process. Using the image-based diffraction based measurement systems described herein, very compact targets can be provided, so that such measurements do not unduly impact the space available for functional product features on the same substrate.

The concepts of asymmetry measurement using the instrument of FIG. 3 are described for example in published patent application US2006066855A1 cited above. Simply stated, while the positions of the diffraction orders in the diffraction spectrum of the target are determined only by the periodicity of the target, asymmetry of intensity levels in the diffraction spectrum is indicative of asymmetry in the individual features which make up the target. In the instrument of FIG. 3, where detector 19 may be an image sensor, such asymmetry in the diffraction orders appears directly as asymmetry in the pupil image recorded by detector 19. This asymmetry can be measured by digital image processing in unit PU, and from this, focus can be determined.

The principles of this measurement are well established, and do not need to be described further herein. However, what will be apparent is that, if any error is present in the measurement of asymmetry of either or both gratings, then the overlay or focus measurement calculated function of those asymmetries is also likely to contain errors.

As mentioned, a problem with measuring multiple gratings simultaneously as illustrated in FIG. 4 is the issue of measurement field (or measurement spot) non-homogeneity. Existing systems for diffraction based overlay, focus or dose metrology are known to suffer from measurement field non-homogeneity, i.e. the measured (overlay/focus) value is impacted by the location of the grating within the measurement field (often referred to as the measurement spot), that is the field defined by the measurement radiation when measuring the target. This has a negative impact on measurement accuracy and performance.

Each measurement of a grating is typically an intensity measurement. The intensity measurement may be of the intensity of a single diffraction order (e.g., the +1 or −1 order) of radiation diffracted by the grating. It can be shown that the impact of measurement field non-homogeneity is an offset between intensity measurement at different locations within the measurement field. This is illustrated by the graph of FIG. 5. This shows measured intensity of a diffraction order or asymmetry (intensity difference of complementary non-zero diffraction orders) on the y-axis against the parameter of interest (e.g., focus, dose or overlay) on the x-axis. Two curves are shown, a first curve 500 illustrating the relationship for an example grating in a first measurement location within the measurement field and a second curve 510 illustrating the relationship for the same grating in a second measurement location within the measurement field. As can be seen, relationship 500 and relationship 510 are essentially similar, but separated by an offset δ. It is proposed that this offset is calibrated and corrected.

The proposed method, according to an embodiment, comprises a calibration step and a correction step. The calibration step determines a correction based on the offset δ and the correction step applies the correction to subsequent intensity measurements.

In an embodiment, the calibration step comprises performing at least a first measurement and a second measurement of each grating, to obtain respectively a first measurement value Iref. and a second measurement value Ishift. A first measurement may comprise measuring a grating in its normal location. The normal location may be the location of the grating during a typical measurement of a target. This normal location may be the location of the grating when the target of which the grating is comprised is substantially centered within the measurement field. This normal location for each grating may therefore be the location of each grating with respect to the measurement field as illustrated in FIG. 4A. In an embodiment, this first measurement can be performed simultaneously for all gratings comprised within a target.

A second measurement of each grating is performed for each grating, with the grating being measured at the "normal" location of another, similarly oriented grating of the target. In an embodiment, the target comprises pairs of corresponding gratings. By way of example, where the target is an overlay target, a pair of corresponding gratings may comprise two gratings with the same orientation and different biases (e.g., complementary biases, —biases of equal magnitude and opposite direction). The gratings may instead have normal or mirrored features or different target dimensions. In a specific example, a target may comprise four gratings, arranged in two pairs of corresponding gratings. The two pairs of corresponding gratings may comprise a first pair of gratings having a first orientation and a second pair of gratings having a second orientation. The first and second orientations may differ by 90° (e.g., a pair of x-oriented or horizontal gratings and a pair of y-oriented or vertical gratings) or by 180° (e.g. a pair of normal gratings and a pair of mirror gratings).

For focus and/or dose gratings, corresponding gratings may be those which comprise similar grating feature dimensions, such that a target may comprise a first pair of gratings having a first set of grating feature dimensions and a second pair of gratings having a second set of grating feature dimensions. A single feature of a grating structure may comprise a line with high resolution substructures extending perpendicularly from one side of the line. The high resolution substructures on top of a base pitch creates an asymmetric resist profile for each grating feature, with the degree of asymmetry being dependent upon focus/dose. Varying grating feature dimensions such as the line width, high resolution substructure length and/or high resolution substructure width provide different printing properties, and therefore different focus and/or dose response.

Each pair of corresponding gratings may comprise one grating having normal features and a second grating having mirror features. Mirror features may comprise grating features which are laterally inverted relative to the normal features. This may be such that the second grating is substantially similar to the first grating oriented 180° relative to the first grating. Normal and mirror gratings react similarly to certain aberrations (e.g., coma) but have opposite focus dependent asymmetry sensitivity. Therefore the difference signal will be focus sensitive, but not coma sensitive.

Therefore, it should be understood that, in general, the concept of a pair of corresponding gratings may comprise gratings which correspond in terms of any one or more features of the gratings: including (non-exhaustively): orientation, any one or more grating feature dimensions, pairs of master and slave gratings, offset bias, duty cycle, pitch, mark/space ratio.

It should also be understood that concepts disclosed herein are equally applicable to targets comprising more or fewer than four gratings. For example, a target may comprise a single (corresponding) pair of gratings. By way of another example, the target mentioned previously, having a 3×3 array of nine composite gratings, (having, for example, biases −4d, −3d, −2d, −d, 0, +d, +2d, +3d, +4d), can be measured according to the concepts described herein. In such an example, a correction factor would be found per corresponding pair (for example per bias pair—(+4d, −4d); (+3d, −3d); . . . etc) After this, the geometric mean of these corrections can be determined as described below (see Equation (14) or Equation (15)) No correction needs be found for the center grating of this array (without bias in this specific example) as it will be measured in the center of the measurement field in a normal measurement.

In a specific embodiment, each grating of a corresponding pair may be arranged diagonally opposed to the other in a 2×2 array. The normal location of another similarly orientated grating may be the location of the other grating of the corresponding pair when the target is in its typical measuring location, e.g.; the location of the grating when the target of which the grating is comprised is substantially centered within the measurement field.

In this way, a pair of intensity measurement values Iref, Ishift is obtained for each grating: a first measurement value Iref of each grating in its normal location with respect to the measurement field and a second measurement value Ishift of each grating in a shifted location with respect to the measurement field. In each case the shifted location is the normal location of the corresponding similarly orientated grating comprised within the target.

FIGS. 6A-6E illustrate each of these measurements. In FIG. 6A, the target 600 is measured in its normal location, e.g., centered within the measurement field 610. In this way, an intensity measurement value IrefH1, IrefH2, IrefV1, IrefV2 for each component grating H1,H2,V1,V2 is obtained with each of the component gratings H1,H2,V1,V2 in their normal locations. The intensity measurements may be made simultaneously. Note that H and V prefixes for the gratings indicate their orientation (H for horizontal or x-oriented and V for vertical or y-oriented). The specific arrangement shown is purely exemplary and other arrangements and grating ordering is possible, including all alternatives described herein.

Figure 6B:
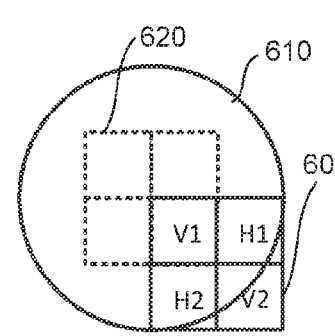

In FIG. 6B, the target 600 is moved within the measurement field 610 such that the grating V1 is in the location within the measurement field 610 occupied by grating V2 when the target 600 is in its normal location (as illustrated in FIG. 6A). Note that FIGS. 6B-6E show (dotted) the normal target location 620 for clarity. With the target 600 in this location with respect to the measurement field 610, an intensity measurement for grating V1 is performed to obtain intensity measurement value IshiftV1.

Figure 6C:
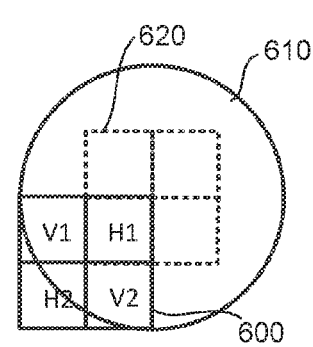

In FIG. 6C, the target 600 is moved within the measurement field 610 such that the grating H1 is in the location within the measurement field 610 occupied by grating H2 when the target 600 is in its normal location. With the target 600 in this location with respect to the measurement field 610, an intensity measurement for grating H1 is performed to obtain intensity measurement value IshiftH1.

Figure 6D:
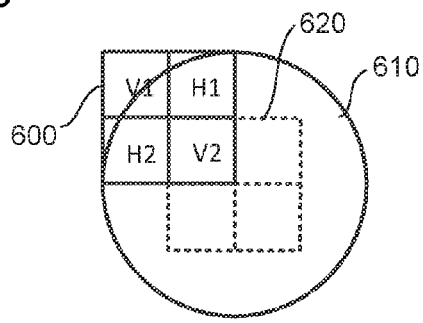

In FIG. 6D, the target 600 is moved within the measurement field 610 such that the grating V2 is in the location within the measurement field 610 occupied by grating V1 when the target 600 is in its normal location. With the target 600 in this location with respect to the measurement field 610, an intensity measurement for grating V2 is performed to obtain intensity measurement value IshiftV2.

Figure 6E:
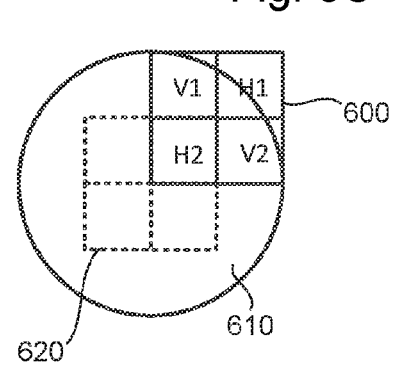

In FIG. 6E, the target 600 is moved within the measurement field 610 such that the grating H2 is in the location within the measurement field 610 occupied by grating H1 when the target 600 is in its normal location. With the target 600 in this location with respect to the measurement field 610, an intensity measurement for grating H2 is performed to obtain intensity measurement value IshiftH2.

FIGS. 7A-7F an alternative calibration stage, for targets where corresponding gratings H1 and H2 or V1 and V2 are arranged side-by-side (adjacent in the x-direction). In FIG. 7A, the target 700 is measured in its normal location, e.g., centered within the measurement field 710. In this way, an intensity measurement value IrefH1, IrefH2, IrefV1, IrefV2 for each component grating H1,H2,V1,V2 is obtained with each of the component gratings H1,H2,V1,V2 in their normal locations. The intensity measurements may be made simultaneously. This step is therefore essentially the same as that illustrated by FIG. 6A, differing only in the target layout.

In FIG. 7B, the target 700 is moved within the measurement field 710 such that the grating V2 is in the location within the measurement field 710 occupied by grating V1 when the target 700 is in its normal location and the grating H2 is in the location within the measurement field 710 occupied by grating H1 when the target 700 is in its normal location. Note that FIGS. 7B and 7C show (dotted) the normal target location 720 for clarity. With the target 700 in this location with respect to the measurement field 710, an intensity measurement for grating V2 is performed to obtain intensity measurement value IshiftV2 and an intensity measurement for grating H2 is performed to obtain intensity measurement value IshiftH2.

In FIG. 7B, the target 700 is moved within the measurement field 710 such that the grating V1 is in the location within the measurement field 710 occupied by grating V2 when the target 700 is in its normal location and the grating H1 is in the location within the measurement field 710 occupied by grating H2 when the target 700 is in its normal location. With the target 700 in this location with respect to the measurement field 710, an intensity measurement for grating V1 is performed to obtain intensity measurement value IshiftV1 and an intensity measurement for grating H1 is performed to obtain intensity measurement value IshiftH1.

In this way, the calibration time is essentially halved compared to the first described calibration embodiment. The target needs only be measured in two shifted locations with respect to the measurement field, with two simultaneous measurements taken for each shifted location.

FIGS. 7D-7F show a similar arrangement but with corresponding gratings being arranged adjacent each other in the y-direction. FIG. 7D illustrates a step essentially the same as that illustrated by FIG. 7A, differing only in the target layout. Similarly, FIG. 7E illustrates a step essentially the same as that illustrated by FIG. 7B except that the shift is down instead of left (from the perspective shown) and FIG. 7F illustrates a step essentially the same as that illustrated by FIG. 7C except that the shift is up instead of right.

Where the target is an overlay target for measuring overlay, grating H1 may be a horizontally oriented grating with a first bias (e.g., positive bias +d), grating H2 may be a horizontally oriented grating with a second bias (e.g., negative bias −d), grating V1 may be a vertically oriented grating with the first bias and grating V2 may be a vertically oriented grating with the second bias. In this way, each grating is measured in its normal location and in the normal location of the similarly oriented grating having a different bias.

Where the target is a focus target for measuring focus and/or dose setting, grating H1 may be a grating having a first set of grating feature dimensions and normal features, grating H2 may be a grating having the first set of grating feature dimensions and mirror features, grating V1 may be a grating having a second set of grating feature dimensions and normal features and grating V2 may be a grating having a second set of grating feature dimensions and mirror features. In this way, each grating is measured in its normal location and in the normal location of the grating with similar grating feature dimensions having opposite feature direction. Other arrangements are possible.

In each case, the calibration stage is completed by determination of a correction, for example a correction factor or correction offset, from each pair of intensity measurement values Iref, Ishift. This correction can then be used in a correction stage to correct the measured values of gratings in their normal location with respect to the measurement field.

In a specific embodiment, the calibration stage may comprise obtaining a value for an offset, to be applied to a grating measurement. This approach is particularly suited to focus/dose targets although is not limited to such. The analysis below is therefore described in relation to focus/dose gratings with normal features (n gratings) and mirrored features (m gratings). Using FIGS. 6A-6E for reference, the normal gratings are those labeled H1 and V1 and the mirror gratings are those labeled H2 and V2.

It can be shown that the measurement field profiles of the n and m gratings are very similar. Suppose now that, due to the measurement field profile, the intensity of grating H1 at the normal location has an offset $\alpha$ and at the shifted location has an offset $\beta$. Where measurements are made in WR mode, the measured asymmetry AH1 of grating H1 and the measured asymmetry AH2 of grating H2 be obtained in a normal measurement by:

$$A_{H1} = (I_{H1,WR0} + \alpha) - (I_{H1,WR180} + \beta)$$

$$A_{H2} = (I_{H2,WR0} + \beta) - (I_{H2,WR180} + \alpha) \quad \text{Equations (4)}$$

where $I_{H1,WR0}$ is the intensity measurement of grating H1 with wafer orientation of 0°, $I_{H1,WR180}$ is the intensity measurement of grating H1 with wafer orientation of 180°, $I_{H2,WR0}$ is the intensity measurement of grating H2 with wafer orientation of 0° and $I_{H2,WR180}$ is the intensity measurement of grating H2 with wafer orientation of 180°. It is assumed that offsets for normal and mirrored gratings are similar.

To reduce aberration effects from the lithographic apparatus, the asymmetries of the n and m targets are averaged:

$$A = \frac{A_{H1} - A_{H2}}{2} \quad \text{Equation (5)}$$

$$= \frac{(I_{H1,WR0} + \alpha) - (I_{H1,WR180} + \beta) - (I_{H2,WR0} + \beta) - (I_{H2,WR180} + \alpha)}{2}$$

$$= \frac{I_{H1,WR0} - I_{H1,WR180} - I_{H2,WR0} - I_{H2,WR180} + 2(\alpha - \beta)}{2}$$

It should be noted that the results should be subtracted as otherwise the intensity measurements from the H1 and H2 gratings will cancel due to the orientation of the teeth of the grating features. It becomes clear from Equation (5) that the measurement field dependent effects do not cancel in this measurement.

Now considering the situation where calibration measurements are included:

$$A_{H1,n} = (I_{H1,WR0,n} + \alpha) - (I_{H1,WR180,n} + \beta) \quad \text{Equation (6)}$$

$$= (I_{H1,WR0,n} - I_{H1,WR180,n}) + (\alpha - \beta)$$

$$A_{H1,s} = (I_{H1,WR0,s} + \beta) - (I_{H1,WR180,s} + \alpha)$$

$$= (I_{H1,WR0,s} - I_{H1,WR180,s}) - (\alpha - \beta)$$

$$A_{H1} = \frac{A_{H1,n} + A_{H1,s}}{2}$$

$$A_{H1} = \frac{I_{H1,WR0,n} - I_{H1,WR180,n} + I_{H1,WR0,s} - I_{H1,WR180,s}}{2}$$

where the subscript n relates to intensities from normal measurements and subscript s relates to intensities from shifted measurements.

From Equation (6) it becomes clear that when the two asymmetry signals AH1 and AH2 are averaged, the offsets $\alpha, \beta$ cancel. This assumes that the offsets before and after wafer rotation are similar, which is a reasonable assumption. Consequently, it can be seen that the effects of measurement field non-homogeneity can be removed if shifted measurements are performed next to normal measurements. However, these extra measurements would lead to unacceptable measurement throughput times if performed for each measurement. Consequently, the shifted measurements are performed less frequently in a calibration stage (the frequency of calibration is at the user's discretion). In this embodiment, the calibration stage comprises determining an offset between the intensity measured at the normal location and the average intensity. The correction stage then comprises subsequently correcting the normal measurements with this calibrated offset. This calibration may be performed optionally per grating; and may also be performed per aperture and/or per wafer orientation. The calibration in this embodiment is as follows:

$$I_{H1,WR0,n} = I_{H1,WR0} + \alpha \quad \text{Equations (7)}$$

-continued $$I_{H1,WR0,s} = I_{H1,WR0} + \beta$$

$$I_{H1,WR180,n} = I_{H1,WR0} + \beta$$

$$I_{H1,WR180,s} = I_{H1,WR0} + \alpha$$

$$I_{H1,WR0,av} = \frac{I_{H1,WR0,n} - I_{H1,WR0,s}}{2} = I_{H1,WR0,n} + \frac{\alpha + \beta}{2}$$

$$I_{H1,WR180,av} =$$

$$\frac{I_{H1,WR180,n} - I_{H1,WR180,s}}{2} = I_{H1,WR180,n} + \frac{\alpha + \beta}{2}$$

where subscript av indicates an average intensity.

It should be noted that the +1st and −1st order intensities are still impacted by measurement field non-homogeneity, even after calibration. However, as asymmetry measurements comprises the difference between the two intensities, the offset terms α,β are cancelled in the asymmetry measurements. Therefore the calibration stage in this embodiment comprises determining the offset Δ between the normal measurement and the average measurement:

$$I_{av} = \frac{I_n + I_s}{2} \quad \text{Equation (8)}$$

$$I_n = I_{av} + \Delta$$

This offset can be therefore be determined from the normal and shifted measurements obtained in the calibration stage using:

$$\Delta = \frac{I_n - I_s}{2} \quad \text{Equation (9)}$$

The correction can be, in principle, determined as a function of various parameters of the grating and/or the measurement device. These parameters may comprise, for example, one or more of: grating type (e.g., bias or grating feature dimensions), wafer rotation angle (e.g., two angles 180° apart) and aperture (e.g., aperture labeled 13N or labeled 13S in FIG. 3A). This comprises performing the calibration (normal measurement and shifted measurement) under different sets of conditions (grating type, wafer rotation angle and aperture profile), and in each case, determining a correction (here a correction offset although this concept is applicable to other correction methods disclosed herein) specific to those conditions. In an embodiment (described in more detail below) the some or all of these corrections may be averaged to reduce noise or find (for example) an average correction for a specific parameter (e.g. an average correction for the different grating types).

The correction offset Δ may then be used to correct individual measurements in a correction stage. This can be done by applying the correction offset to the measured signal (e.g., intensity) value. Application of the offset may comprise adding or subtracting the correction offset from the measured signal as appropriate. Specifically, based on Equation (8), a corrected intensity value Î can be found from:

$$\hat{I} = I - \Delta \quad \text{Equation (10)}$$

where I is the measured intensity value with the grating in the normal location (target centered in measurement field such that all gratings can be measured simultaneously).

In an embodiment, where multiple corrections are determined for different conditions, the appropriate determined correction should be selected for the (e.g., illumination) conditions used in obtaining the measured intensity value. In such an embodiment, the correction used in the correction step will have been determined from normal and shifted measurements obtained under the same conditions as those used to obtain the measured intensity value being corrected.

In another specific embodiment, particularly suited to overlay targets although not limited to such, instead of a correction offset, the correction may comprise determining a correction factor CF. The correction factor can be calculated using each pair of intensity measurement values $I_{ref}$, $I_{shift}$ corresponding to a grating. In such an embodiment, the correction factor CF for a grating can be calculated by:

$$CF = 1 + \frac{I_{shift} - I_{ref}}{2I_{ref}} = \frac{I_{shift} + I_{ref}}{2I_{ref}} \quad \text{Equation (11)}$$

Application of the correction factor CF will therefore impose a correction on the measured intensity value such that the corrected intensity value is substantially that which would be measured had the grating been centered between the normal location and shifted location; where the corresponding targets are diagonally opposed, this would mean centered within the measurement field.

Where it is possible to determine the target location x0, for example where it is possible to use pattern recognition techniques, the correction factor can be determined with a greater degree of accuracy. A non-zero location xo would mean that the target is not ideally centered with respect to the measurement field. In such a case, the correction factor CF can be calculated by:

$$CF = 1 + \frac{\frac{\Delta x}{2} - x_0}{\frac{\Delta x}{2}} \cdot \frac{I_{shift} + I_{ref}}{2I_{ref}} \quad \text{Equation (12)}$$

where Δx is the distance between the reference location and shifted location.

Following the calibration stage to determine the correction factor, the correction factor may then be used to correct individual measurements in a correction stage. This can be done by multiplying the correction factor with the measured signal (e.g., intensity) value. Specifically, a corrected intensity value Î can be found using:

$$\hat{I} = CF \cdot I \quad \text{Equation (13)}$$

where I is the measured intensity value with the grating in the normal location (target centered in measurement field such that all gratings can be measured simultaneously). The correction factor CF may be any of the averaged correction factors $\overline{CF}$ described below. The appropriate correction factor should be selected for the (e.g., illumination) conditions used in obtaining the measured intensity value I.

As with the correction offset, the correction factor CF can be, in principle, determined as a function of various parameters of the grating and/or the measurement device. These parameters may comprise, for example, one or more of: grating type (e.g., bias or grating feature dimensions), wafer rotation angle (e.g., two angles 180° apart) and aperture profile (e.g., aperture labeled 13N or labeled 13S in FIG. 3A). This can be done by performing further pairs of measurements of gratings at normal and shifted locations to obtain further correction factors, the further pairs of measurements being performed under different conditions. The different conditions may comprise variations of a single parameter, or different combinations of multiple varied parameters.

For example (applicable to any type of correction including correction offset and correction factor), a grating can be measured at normal and shifted locations under a first condition and then can be measured at normal and shifted locations under a second condition. A correction can then be calculated for each pair of measurements. This can be repeated for any number of conditions, for one or more parameters. For the purposes of noise suppression, an averaged correction can be determined as an average $\overline{C}$ of the corrections C for each pair of measurements performed under a different condition. The average may be a geometric mean, for example:

$$\overline{C} = \sqrt[n]{C(\text{condition}1) \cdot C(\text{condition}2) \ldots \cdot C(\text{condition}n)} \quad \text{Equation (14)}$$

The actual number of measurement conditions may be chosen to suit a specific correction (i.e., a specific non-ideality of the measurement device of which it would be desirable to suppress). At the same time, the number of measurement conditions will determine the number of measurements which need to be made and therefore the measurement throughput. If a very fast throughput is required, then only a single correction need be determined to correct for illumination non-uniformity. This single correction is determined for a single grating bias or grating type measured using a single illumination condition. To improve noise suppression, two different gratings can be measured. For example, a grating having a positive bias +d can be measured to determine correction C(+d) and a grating having a negative bias −d can be measured to determine correction C(−d). It should be noted that this averaging is equally applicable to other grating types, for example normal and mirrored gratings or gratings which differ in their grating feature dimensions. The averaged correction would then be:

$$\overline{C} = \sqrt{C(+d) \cdot C(-d)} \quad \text{Equation (15)}$$

This averaged correction may be used as the correction for all illumination conditions. Alternatively, different illumination conditions can be taken into account when determining the correction. In an embodiment, a correction is determined for each wafer rotation angle (0° and 180°), for example when performing an asymmetry measurement in wafer rotation mode. This can be done for a single grating type (measurement made for each wafer rotation angle), or can be done with the noise suppression measured previously (measurements made for each of: two grating types and two wafer rotation angles). In the latter case, assuming that different grating types are gratings with equal and opposite biases +d, −d as before, the corrections C(0°), C(180°) may be calculated by:

$$\overline{C}(0°) = \sqrt{C(+d, 0°) \cdot C(-d, 0°)}$$

$$\overline{C}(180°) = \sqrt{C(+d, 180°) \cdot C(-d, 180°)} \quad \text{Equations (16)}$$

where C(+d, 0°) is a correction determined for a grating type having a bias +d measured at wafer rotation angle 0°, C(−d, 0°) is a correction determined for a grating type having a bias −d measured at wafer rotation angle 0°, C(+d, 180°) is a correction determined for a grating type having a bias +d measured at wafer rotation angle 180° and C(−d, 180°) is a correction determined for a grating type having a bias −d measured at wafer rotation angle 180°.

Additionally, corrections may be determined for different illumination aperture profiles (for example when measuring asymmetry in complementary aperture mode). This can be done independently of wafer rotation angle and/or noise suppression. However, in another embodiment, four corrections are determined, one for a different illumination condition comprising a different combination of each wafer rotation angle and illumination aperture profile. As before, the wafer rotation angle may be one of 0° and 180°, while the illumination aperture profile may be one of those labeled 13N or labeled 13S in FIG. 3A. Where this is done with improved noise suppression, measurements will be made for each of two grating types, two wafer rotation angles and two illumination aperture profiles.

The frequency at which calibrations (to obtain corrections) are performed using the methods described, is at the user's discretion. This will usually be a compromise between correction accuracy and measurement throughput. The more calibrations which are performed (and the more measurements made per calibration), the more accurate the corrections will be, although this will come at a throughput cost. By way of specific example, a calibration can be performed per tool, per product layer, per lot or per wafer or any combination of these It can be seen in FIGS. 6A-6E and FIGS. 7A-7F that, during the second intensity measurement, it may be that the whole target is not within the measurement field. This may mean that some pattern recognition techniques will not be able to be used, and therefore the location of the target with respect to the measurement field may not be directly measurable. To obviate the use of pattern recognition techniques, it is proposed that the method comprises performing a predetermined movement of the location of the target with respect to the measurement field between the first intensity measurement and a second intensity measurement, and similarly between each subsequent second intensity measurement for each grating. The predetermined movement may be performed without use of pattern recognition techniques. The predetermined movement may also be performed without changing the focus (wafer height with respect to the measurement device's optics). This means time is saved in not waiting for the focus/leveling subsystem to settle. It also helps ensure similar measurement conditions for the first measurement and each second measurement.

In a particular example, to shorten measurement time, the predetermined movements will move directly between each second measurement. That is, there will be direct predetermined movements between the arrangements illustrated in (for example) FIG. 6B, FIG. 6C, FIG. 6D and FIG. 6E without centering between each second measurement. However, in another embodiment, the target can be centered between each (or one or some) of these movements, so as to compensate for accumulating positioning error in case of applying a multitude of such predetermined moves, for example in the 3×3 multi-bias example described above.

It should be appreciated that all description of movement of the target or grating with respect to, or within, the measurement field includes moving the target or grating while maintaining the measurement field (projection optics) stationary, moving the measurement field (projection optics) while maintaining the target/grating stationary or moving both the target/grating and measurement field (projection optics) in synchronization.

FIG. 8 is a flowchart of the steps of a method for measuring a parameter of a lithographic process from target asymmetry according to an exemplary embodiment. The steps are as follows, and are then described in greater detail thereafter:

800—a Start.
805—Calibration
   810—Perform first measurement of periodic structures (gratings) at normal measurement location;
   820—Perform second measurement of periodic structures (gratings) at shifted measurement location;
   830—Determine a correction from said first measurement and said second measurement, for each grating;
   840—Optionally determine further corrections for different measurement conditions or grating types;
   845—Correction
   850—Perform measurements of radiation scattered from each grating to obtain measured values of radiation scattered from each grating;
   860—Correct measured values of radiation scattered from each grating by applying the applicable correction;
   870—Determine asymmetry in each grating from corrected values of radiation scattered from each grating;
   880—Determine parameter of lithographic process from determined asymmetry;
890—End.

Calibration stage 805 comprises calibration steps 810-840. Calibration stage 805 can be performed at any frequency, for example per tool, per product layer, per lot or per wafer or any combination of these.

At step 810, a first measurement of the gratings is performed at the normal measurement location. The normal measurement location may be the target being centered within the measurement field, as has been described. This first measurement may comprise a measurement of intensity of a zeroth or non-zeroth diffraction order of radiation scattered by the grating.

At step 820, a second measurement of the gratings is performed at the shifted measurement location. The shifted measurement location may be the normal measurement location of a corresponding, similarly oriented grating of the same target, as has been described. Again, this first measurement may comprise a measurement of intensity of a zeroth or non-zeroth diffraction order of radiation scattered by the grating.

At step 830, a correction is determined from the first and second measurements determined at step 810 and step 820. This step may use Equation (9), Equation (11) or Equation (12), for example.

At optional step 840, further corrections may be determined for different conditions or grating types. These further corrections may be averaged, or may be applicable to a certain condition used (for example, an illumination condition). In the latter case illumination condition specific corrections may be determined, such that the applicable illumination condition specific correction is used in the correction stage depending on the illumination condition. This step may use Equation (14), Equation (15) or Equation (16), for example.

Following the calibration stage, a correction stage 845 is performed to correct measurements for the effects of measurement field non-homogeneity.

At step 850, measurements of each grating, e.g., intensity measurements of complementary non-zero orders of diffracted radiation scattered by each grating, are made with the target in its normal measurement location (e.g., centered within the measurement field). The complementary non-zero orders of diffracted radiation may be obtained in either wafer rotation mode or complementary aperture mode.

At step 860, the applicable correction as determined during calibration stage 805, is applied to intensity measurements, depending on grating location and (optionally) other conditions, such as the illumination condition used. This step may use Equation (10) or Equation (13), for example.

At step 870, asymmetry in each grating is determined from the corrected intensity measurements. Equation (1) may be used in this step.

At step 880, the parameter being monitored can be calculated from the determined asymmetry. The parameter may be, for example, focus, dose or overlay. Where the parameter is overlay, this step may use Equation (3).

The proposed method is believed to be effective, regardless of the source of non-homogeneity in the measurement field. Additionally, it does not rely on an assumption/model for the cause of the measurement field non-homogeneity. The proposed method can be used in either wafer rotation or complementary aperture mode, and does not rely on a measurement using different apertures. The proposed method is flexible in the sense that the proposed calibration step can be performed either a) per target b) per wafer c) per wafer lot. The calibrated correction is largely target independent, which allows (periodic, drift) measurement from a i) fiducial target, ii) test wafer or iii) an actual wafer. The proposed method can cope with targets that are partially outside of the measurement field (during the calibration), by using target displacements without a subsequent pattern recognition, or with a subsequent pattern recognition/image correlation on the basis of individual gratings.

The proposed concept is described in terms of correcting intensities of higher order diffracted radiation. However, it should be appreciated that the concept is equally applicable to corrections of any measurements affected by measurement field non-homogeneity. Therefore, corrections of zeroth order diffracted radiation, used for example in CD (critical dimension) measurements, can be determined using the methods and apparatuses described herein. Such corrections may therefore be of pupil plane (non-dark-field) measurements.

The correction has been described as being a correction offset or correction factor. However, it should be appreciated that the correction may take other forms, and may for example be a non-linear correction.

While specific embodiments of the invention have been described above, it will be appreciated that the invention may be practiced otherwise than as described.

The above concepts can be applied to diffraction based overlay targets in both dual-layer and multi-layer applications. It can also be applied to diffraction based focus targets for measuring exposure focus and/or targets for measuring dose.

The calculation of corrections above is applied at the stage of calculating asymmetry, before combining asymmetry values to calculate a parameter of interest such as overlay. The techniques described above can be performed to calibrate and then correct the asymmetry measurements, according to the performance of the tool optical system in different modes of illumination and/or imaging. If the measurement process uses different wavelengths and/or polarizations of radiation, then calibration can be performed for these separately.

While the inspection apparatus or tool illustrated in the embodiments comprises a particular form of scatterometer having first and second branches for simultaneous imaging of pupil plane and substrate plane by parallel image sensors, alternative arrangements are possible. Rather than provide two branches permanently coupled to objective lens 16 with beam splitter 17, the branches could be coupled selectively by a movable optical element such as a mirror. The optical system could be made having a single image sensor, the optical path to the sensor being is reconfigured by movable elements to serve as a pupil plane image sensor and then a substrate plane image sensor.

It should be appreciated that the concepts and corrections described herein are equally applicable to measurements obtained in the intermediate pupil plane or the pupil plane (i.e., using either measurement branch of the apparatus of FIG. 3). Pupil plane measurements may, for example, include measurement of critical dimension from a target using zeroth order radiation scattered from the target.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the inspection apparatus hardware and suitable periodic structures of the targets as realized on substrates and patterning devices, an embodiment may include a computer program containing one or more sequences of machine-readable instructions implementing methods of measurement of the type illustrated above to obtain information about a lithographic process. This computer program may be executed for example within controller PU in the apparatus of FIG. 3 and/or the control unit LACU of FIG. 2. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the invention are described in below numbered clauses:

1. A method of determining a correction for measured values of radiation diffracted from a target subsequent to measurement of the target using measurement radiation defining a measurement field, said correction correcting for measurement field location dependence in said measured values, said target comprising a plurality of periodic structures; wherein said method comprises:

performing a first measurement and a second measurement of at least one of said periodic structures; and determining a correction from said first measurement and said second measurement; wherein said first measurement is performed with said target being in a normal measurement location with respect to the measurement field; and said second measurement is performed with the periodic structure in a shifted location with respect to the measurement field, said shifted location comprising the location of another of said periodic structures when said target is in said normal measurement location with respect to the measurement field.

2. A method according to clause 1 wherein the periodic structure being measured and said another of said periodic structures are similarly oriented.

3. A method according to clause 1 or 2 wherein the periodic structure being measured and said another of said periodic structures comprise similar grating feature dimensions.

4. A method according to clause 1, 2 or 3 wherein said target comprises one or more pairs of corresponding periodic structures, and said method is performed for each pair of corresponding periodic structures such that, where the first measurement is a measurement of one of said pairs of corresponding periodic structures, said shifted location is the location of the other of that pair of corresponding periodic structures when said target is in said normal measurement location with respect to the measurement field.

5. A method according to clause 4 wherein said target comprises two pairs of corresponding periodic structures.

6. A method according to clause 5 wherein said two pairs of corresponding periodic structures are arranged in a two-by-two array.

7. A method according to clause 6 wherein the periodic structures comprised within each of said pairs of corresponding periodic structures are located diagonally opposed in said array.

8. A method according to clause 6 wherein the periodic structures comprised within each of said pairs of corresponding periodic structures are located adjacent each other in said array.

9. A method according to clause 8 wherein a second measurement is performed simultaneously for two periodic structures in their shifted locations.

10. A method according to any of clauses 5 to 9 wherein one of said two pairs of corresponding periodic structures has a first orientation and the other of said two pairs of corresponding periodic structures has a second orientation.

11. A method according to any of clauses 5 to 9 wherein one of said two pairs of corresponding periodic structures has a first set of grating feature dimensions and the other of said two pairs of corresponding periodic structures has a second set of grating feature dimensions 12. A method according to any of clauses 4 to 11 wherein each of said pairs of corresponding periodic structures comprise two periodic structures of two or more layers, each of the two periodic structures having the same orientation and but a different bias between the placement of two of said layers.

13. A method according to any preceding clause wherein said correction is a correction factor being operable to correct for measurement field location dependence in said measured values by multiplying with said measured values.

14. A method according to any preceding clause wherein said correction is a correction offset being operable to correct for measurement field location dependence in said measured values by addition to, or subtraction from, said measured values.

15. A method according to any preceding clause wherein said first measurement comprises measuring all the periodic structures comprised within the target simultaneously.

16. A method according to any preceding clause comprising the step of performing a predetermined move of the target with respect to the measurement field between the normal measurement location for performing the first measurement and the first shifted location for performing said second measurement.

17. A method according to clause 16 comprising performing a plurality of second measurements to respectively measure each periodic structure comprised within a target in the applicable shifted location for that periodic structure, said method comprising the steps of performing a predetermined movement of the target with respect to the measurement field between each of the shifted locations.

18. A method according to clause 16 or 17 wherein each of said predetermined movements is performed without using pattern recognition and without changing focusing of measurement optics.

19. A method according to any preceding clause wherein said target comprises one or more focus gratings for measuring focus.

20. A method according to any preceding clause wherein said target comprises one or more dose gratings for measuring dose.

21. A method according to any preceding clause wherein said target comprises one or more gratings for measuring critical dimension.

22. A method according to any of clauses 1 to 19 wherein said target is an overlay target for measuring overlay.

23. A method according to any preceding clause wherein application of the correction on a measured value of a periodic structure, measured in a location which is not centered with respect to the measurement field, corrects said measured value such that the corrected value is substantially that which would have been obtained if said periodic structure had been measured in a location centered between said normal measurement location and said shifted location.

24. A method according to any preceding clause comprising measuring the actual target location with respect to the measurement field during the first measurement and second measurement and using these measurements of the target location in determining the correction such that it better corrects said measured value to that which would have been obtained if said periodic structure had been measured in a location centered with respect to the measurement field.

25. A method according to any preceding clause wherein the correction is determined as a function of one or more parameters of the periodic structure and/or a measurement device used to perform said first measurement and second measurement.

26. A method according to any preceding clause wherein plural parameter dependent corrections, applicable to a single location within the measurement field, are determined, each one for a different parameter condition.

27. A method according to clause 26 comprising calculating an average of the parameter dependent corrections to obtain a noise suppressed parameter dependent correction.

28. A method according to clause 26 or 27 wherein a parameter on which said parameter dependent correction is dependent comprises overlay bias of the periodic structure.

29. A method according to clause 26, 27 or 28 wherein said different parameter condition may comprise a different illumination condition, said different illumination condition comprising the use of a different illumination aperture profile for the measurement radiation and/or a different substrate orientation with respect to measurement radiation, said target being comprised on said substrate.

30. A method according to any preceding clause comprising applying said correction to a measured value of radiation scattered by a periodic structure.

31. A method according to any of clauses 1 to 29 wherein a plurality of corrections are determined, each one applicable to the location of a periodic structure comprised within a target when said target is in said normal measurement location with respect to the measurement field.

32. A method according to clause 31 comprising the step of applying an applicable correction to a measured value of radiation scattered by a periodic structure, the applicable correction depending at least on the location of said periodic structure with respect to the measurement field.

33. A method of measuring a target comprising a plurality of periodic structures, said method comprising:
simultaneously measuring each periodic structure of said target thereby obtaining for each periodic structure a measured value of radiation scattered by the periodic structure; and
using a correction applicable to the location of the periodic structure for which the measured intensity value corresponds, to correct each measured value of radiation scattered by the periodic structure so as to compensate for the effects of measurement field location dependence in the measured values;
wherein each correction is determined using the method of any of clauses 1 to 29.

34. A method of measuring asymmetry in a target comprising a plurality of periodic structures formed by a lithographic process on a substrate, the method comprising the steps of:
a first measurement step comprising forming and detecting a first image of each of the periodic structures while illuminating the target with measurement radiation, the first image being formed using a first selected part of radiation diffracted by each periodic structure, thereby obtaining a first measured value of radiation scattered by each periodic structure;
a second measurement step comprising forming and detecting a second image of each of the periodic structures while illuminating the target with measurement radiation, the second image being formed using a second selected part of radiation diffracted by each periodic structure, thereby obtaining a second measured value of radiation scattered by each periodic structure, said second selected part of radiation being symmetrically opposite to the first part, in a diffraction spectrum of the periodic structure; and
calculating a measurement of asymmetry in each periodic structure based on the applicable first measured value of radiation scattered by the periodic structure and second measured value of radiation scattered by the periodic structure,
wherein in the step of calculating the asymmetry measurement, a correction to compensate for the effects of measurement field location dependence in the measured values of radiation scattered by the periodic structure is performed using a correction determined using the method of any of clauses 1 to 29.

35. A method according to clause 34 wherein said substrate is rotated through 180° between said first measurement and said second measurement, so as to have said first image formed by said first selected part of radiation diffracted by each periodic structure and said second image formed by said second selected part of radiation diffracted by each periodic structure.

36. A method according to clause 34 wherein the aperture profile of said measurement radiation is changed between said first measurement and said second measurement, so as to have said first image formed by said first selected part of radiation diffracted by each periodic structure and said second image formed by said second selected part of radiation diffracted by each periodic structure.

37. A method according to clause 34 wherein the said first image formed by said first selected part of radiation diffracted by each periodic structure and said second image formed by said second selected part of radiation diffracted by each periodic structure is obtained without a change in substrate orientation or aperture profile between acquisition of the first image and second image, said targets comprising mirrored gratings and/or dual gratings.

38. A method according to any of clauses 34 to 37 wherein said first selected part of radiation diffracted by each periodic structure and said second selected part of radiation diffracted by each periodic structure comprise complementary non-zeroth diffraction orders.

39. A method of measuring a target parameter of one or more periodic structures comprised within a target, said method comprising:

forming and detecting an image of each periodic structure while illuminating the target with measurement radiation, the image being formed using radiation scattered by each periodic structure, thereby obtaining a first measured value of radiation scattered by each periodic structure;

calculating a measurement of said target parameter for each periodic structure from the corresponding image;

wherein in the step of calculating measurement of said target parameter, a correction to compensate for the effects of measurement field location dependence in the measured values of radiation scattered by the periodic structure is performed using a correction determined using the method of any of clauses 1 to 23.

40. A method according to clause 39 wherein said target parameter is critical dimension.

41. A metrology apparatus for measuring a parameter of a lithographic process, the metrology apparatus being operable to perform the method of any of clauses 1 to 40.

42. A metrology apparatus according to clause 41 comprising:

a support for said substrate having one or more targets thereon;

an optical system for measuring each target; and a processor operable to determine a correction according to the method of any of clauses 1 to 29.

43. A lithographic system comprising:

a lithographic apparatus comprising:

an illumination optical system arranged to illuminate a pattern;

a projection optical system arranged to project an image of the pattern onto a substrate; and a metrology apparatus according to clause 41 or 42, wherein the lithographic apparatus is arranged to use a determined parameter value calculated by the metrology apparatus in applying the pattern to further substrates, wherein said determined parameter value is determined using intensity measurements made using said metrology apparatus and to which said correction has been applied.

44. A computer program comprising processor readable instructions which, when run on suitable processor controlled apparatus, cause the processor controlled apparatus to perform the method of any one of clauses 1 to 37.

45. A computer program carrier comprising the computer program of clause 44.

46. A method of manufacturing devices wherein a device pattern is applied to a series of substrates using a lithographic process, the method including:

using the method of any of clauses 1 to 29 to determine at least one correction, applying the at least one correction to intensity measurements, and using the corrected intensity measurements to monitor a lithographic process parameter, and controlling the lithographic process for later substrates in accordance with the lithographic process parameter.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of determining a correction for measured values of radiation diffracted from a target subsequent to measurement of the target using measurement radiation defining a measurement field, the correction correcting for measurement field location dependence in the measured values, the target comprising a plurality of periodic structures, the method comprising:

performing a first measurement and a second measurement of at least one of the periodic structures; and determining a correction from the first and second measurements; wherein:

the first measurement is performed with the target being in a normal measurement location with respect to the measurement field;

the second measurement is performed with the periodic structure in a shifted location with respect to the measurement field, the shifted location comprising a location of another periodic structure when the target is in the normal measurement location with respect to the measurement field; and the correction is a correction parameter being operable to correct for the measurement field location dependence in the measured values by an adjustment of the measured values.

2. The method as claimed in claim 1, wherein the target comprises one or more pairs of corresponding periodic structures, and the method is performed for each pair of corresponding periodic structures such that, where the first measurement is a measurement of one periodic structure of each pair, the shifted location is the location of the other periodic structure of that pair when said target is in said normal measurement location with respect to the measurement field.

3. The method as claimed in claim 1, wherein the adjustment of the measured values comprises multiplication with the measured values.

4. The method as claimed in claim 1, wherein the adjustment of the measured values comprises addition to, or subtraction from, the measured values.

5. The method as claimed in claim 1, further comprising: performing a predetermined move of the target with respect to the measurement field between the normal measurement location for performing the first measurement and the shifted location for performing the second measurement.

6. The method as claimed in claim 1, wherein the target comprises one or more focus gratings for measuring focus.

7. The method as claimed in claim 1, wherein application of the correction to a measured value of a periodic structure, measured in a location which is not centered with respect to the measurement field, corrects the measured value such that the corrected value is substantially that which would have been obtained if the periodic structure had been measured in a location centered between the normal measurement location and the shifted location.

8. The method as claimed in claim 1, further comprising: measuring an actual target location with respect to the measurement field during the first and second measurements; and
using the first and second measurements of the actual target location in determining the correction such that the correction better corrects the measured values to that which would have been obtained if the periodic structure had been measured in a location centered with respect to the measurement field.

9. The method as claimed in claim 1, further comprising: determining the correction as a function of one or more parameters of the periodic structure and/or a measurement device used to perform the first and second measurements.

10. The method as claimed in claim 1, further comprising: determining a plurality of parameter dependent corrections, applicable to a single location within the measurement field, wherein each parameter dependent correction is for a different parameter condition.

11. The method as claimed in claim 10, further comprising: calculating an average of the plurality of parameter dependent corrections to obtain a noise suppressed parameter dependent correction.

12. The method as claimed in claim 10, wherein a parameter on which the plurality of parameter dependent corrections are is dependent comprises overlay bias of the periodic structure.

13. The method as claimed in claim 10, wherein the different parameter condition comprises a different illumination condition, the different illumination condition comprising a use of a different illumination aperture profile for the measurement radiation and/or a different substrate orientation with respect to measurement radiation, the target being comprised on a substrate with the different substrate orientation.

14. A method of measuring a target comprising a plurality of periodic structures, the method comprising:
simultaneously measuring each periodic structure of the target thereby obtaining, for each periodic structure, a measured value of radiation scattered by the periodic structure; and
using a correction applicable to a location of the periodic structure for which the measured value of radiation corresponds, to correct each measured value of radiation scattered by the periodic structure so as to compensate for the effects of measurement field location dependence in the measured values;
wherein each correction is determined using the method comprising,
performing a first measurement and a second measurement of at least one of the periodic structures; and
determining a correction from the first and second measurements; wherein:
the first measurement is performed with the target being in a normal measurement location with respect to a measurement field;
the second measurement is performed with the at least one periodic structure in a shifted location with respect to the measurement field, the shifted location comprising a location of another periodic structure when the target is in the normal measurement location with respect to the measurement field; and
the correction is a correction parameter being operable to correct for the measurement field location dependence in the measured values by an adjustment of the measured values.

15. A method of measuring asymmetry in a target comprising a plurality of periodic structures formed by a lithographic process on a substrate, the method comprising:
a first measurement step comprising forming and detecting a first image of each of the periodic structures while illuminating the target with measurement radiation, the first image being formed using a first selected part of radiation diffracted by each periodic structure, thereby obtaining a first measured value of radiation scattered by each periodic structure;
a second measurement step comprising forming and detecting a second image of each of the periodic structures while illuminating the target with measurement radiation, the second image being formed using a second selected part of radiation diffracted by each periodic structure, thereby obtaining a second measured value of radiation scattered by each periodic structure, the second selected part of radiation being symmetrically opposite to the first selected part of radiation, in a diffraction spectrum of the periodic structure; and
calculating a measurement of asymmetry in each periodic structure based on the applicable first measured value of radiation scattered by the periodic structure and the second measured value of radiation scattered by the periodic structure,
wherein in the calculating the measurement of asymmetry, a correction to compensate for the effects of measurement field location dependence in the first and second measured values of radiation scattered by the periodic structure is performed using a correction determined using the method comprising,
performing a first measurement and a second measurement of at least one of the periodic structures; and
determining a correction from the first and second measurements; wherein:
the first measurement is performed with the target being in a normal measurement location with respect to a measurement field;
the second measurement is performed with the at least one periodic structure in a shifted location with respect to the measurement field, the shifted location comprising a location of another of said periodic structure when the target is in the normal measurement location with respect to the measurement field; and the correction is a correction parameter being operable to correct for the measurement field location dependence in the first and second measured values by an adjustment of the first and second measured values.

16. A method of measuring a target parameter of one or more periodic structures comprised within a target, the method comprising:
forming and detecting an image of each periodic structure while illuminating the target with measurement radiation, the image being formed using radiation scattered by each periodic structure, thereby obtaining measured values of radiation scattered by each periodic structure;
calculating a measurement of the target parameter for each periodic structure from the corresponding image;
wherein in the step of calculating the measurement of the target parameter, a correction to compensate for effects of measurement field location dependence in measured values of radiation scattered by the periodic structure is performed using a correction determined using a method comprising,
performing a first measurement and a second measurement of at least one of the periodic structures; and
determining a correction from the first and second measurements; wherein:
the first measurement is performed with the target being in a normal measurement location with respect to a measurement field;
the second measurement is performed with the at least one periodic structure in a shifted location with respect to the measurement field, the shifted location comprising a location of another periodic structure when the target is in the normal measurement location with respect to the measurement field; and
the correction is a correction parameter being operable to correct for the measurement field location dependence in the measured values by an adjustment of the measured values.

17. A lithographic system comprising:
a lithographic apparatus comprising:
an illumination optical system arranged to illuminate a pattern;
a projection optical system arranged to project an image of the pattern onto a substrate; and
a metrology apparatus configured to perform a method comprising:
performing a first measurement and a second measurement of at least one periodic structure of a target; and
determining a correction from the first and second measurements; wherein:
the first measurement is performed with the target being in a normal measurement location with respect to a measurement field; and
the second measurement is performed with the at least one periodic structure in a shifted location with respect to the measurement field, the shifted location comprising a location of another periodic structure when the target is in the normal measurement location with respect to the measurement field; and
the correction is a correction parameter being operable to correct for measurement field location dependence in measured values by an adjustment of the measured values,
wherein the lithographic apparatus is arranged to use a determined parameter value calculated by the metrology apparatus in applying the pattern to further substrates,
wherein the determined parameter value is determined using intensity measurements made using the metrology apparatus and to which the correction has been applied.

18. A computer program comprising processor readable instructions which, when run on a suitable processor controlled apparatus, cause the processor controlled apparatus to perform operations comprising:
performing a first measurement and a second measurement of at least one periodic structure of a target; and
determining a correction from the first and second measurements; wherein:
the first measurement is performed with the target being in a normal measurement location with respect to a measurement field; and
the second measurement is performed with the at least one periodic structure in a shifted location with respect to the measurement field, the shifted location comprising a location of another of said periodic structure when the target is in the normal measurement location with respect to the measurement field; and
the correction is a correction parameter being operable to correct for measurement field location dependence in measured values by an adjustment of the measured values.

19. A method of manufacturing devices wherein a device pattern is applied to a series of substrates using a lithographic process, the method comprising:
performing a first measurement and a second measurement of at least one periodic structure of a target;
determining a correction from the first and second measurements; wherein:
the first measurement is performed with the target being in a normal measurement location with respect to a measurement field; and
the second measurement is performed with the at least one periodic structure in a shifted location with respect to the measurement field, the shifted location comprising a location of another periodic structures when the target is in the normal measurement location with respect to the measurement field;
the correction is a correction parameter being operable to correct for measurement field location dependence in measured values by an adjustment of the measured values;
applying the correction to intensity measurements, and using the corrected intensity measurements to monitor a lithographic process parameter; and
controlling the lithographic process for later substrates in accordance with the lithographic process parameter.

* * * * *

UNITED STATES PATENT AND TRADEMARK OFFICE
CERTIFICATE OF CORRECTION

| | |
|---|---|
| PATENT NO. | : 9,958,789 B2 |
| APPLICATION NO. | : 15/186031 |
| DATED | : May 1, 2018 |
| INVENTOR(S) | : Wardenier et al. |

Page 1 of 1

It is certified that error appears in the above-identified patent and that said Letters Patent is hereby corrected as shown below:

In Column 32, Line 64, please delete "location of another of said" and insert --location of another--.

In Column 34, Line 49, please delete "another periodic structures" and insert --another periodic structure--.

Signed and Sealed this
First Day of January, 2019

Andrei Iancu
*Director of the United States Patent and Trademark Office*